(12) United States Patent
Jutras

(10) Patent No.: US 12,263,074 B2
(45) Date of Patent: Apr. 1, 2025

(54) WATERPROOF PROTECTOR FOR A BODY MEMBER

(71) Applicant: Concept H2-ITEX Inc., Brossard (CA)

(72) Inventor: Monique Jutras, Brossard (CA)

(73) Assignee: Concept H2-ITEX Inc., Brossard (CA)

( * ) Notice: Subject to any disclaimer, the term of this patent is extended or adjusted under 35 U.S.C. 154(b) by 232 days.

(21) Appl. No.: 17/859,574

(22) Filed: Jul. 7, 2022

(65) Prior Publication Data

US 2023/0008618 A1 Jan. 12, 2023

Related U.S. Application Data

(60) Provisional application No. 63/219,510, filed on Jul. 8, 2021.

(51) Int. Cl.
*A61F 15/00* (2006.01)
*A41D 31/10* (2019.01)

(52) U.S. Cl.
CPC ............ *A61F 15/004* (2013.01); *A41D 31/10* (2019.02)

(58) Field of Classification Search
CPC ....... A61F 15/004; A61B 46/00; A61B 46/20; A61B 46/27; A61B 46/40; A41D 31/10
See application file for complete search history.

(56) References Cited

U.S. PATENT DOCUMENTS

| | | |
|---|---|---|
| 3,741,203 A | 6/1973 | Liman |
| 4,178,924 A | 12/1979 | Baxter |
| 4,363,317 A | 12/1982 | Broucek |
| 4,523,586 A * | 6/1985 | Couri .................... A61F 13/10 |
| | | D24/190 |
| 4,530,350 A | 7/1985 | Brown et al. |
| 4,562,834 A | 1/1986 | Bates et al. |
| 4,610,245 A | 9/1986 | Biearman |
| 4,986,265 A | 1/1991 | Caponi |
| 5,016,648 A | 5/1991 | Brown et al. |
| 5,063,919 A | 11/1991 | Silverberg |

(Continued)

FOREIGN PATENT DOCUMENTS

| | | |
|---|---|---|
| WO | 2003059234 A1 | 7/2003 |
| WO | 2019241391 A1 | 12/2019 |

OTHER PUBLICATIONS

San Chemicals, Ltd., "MELCO Technical Information", Copyright 2006. (Year: 2006).*

*Primary Examiner* — Keri J Nelson
(74) *Attorney, Agent, or Firm* — Philip A. Swain; Equinox IP Inc.

(57) ABSTRACT

A waterproof protector for a body member and a method for fabricating the waterproof protector. The waterproof protector comprises a body comprising a fabric layer comprising polyester; a water repellent applied to a first surface of the fabric layer; an antimicrobial substance applied to an opposite surface of the fabric layer and located on an inner surface of the body. The body comprises a main seam formed by a junction of the fabric layer, the junction being sewn by an ultrasound to form a main seam which is further sealed with an additional layer of a waterproof material positioned on the inner surface of the body and sealed to the inner surface by heat. The waterproof protector further comprises a stretchable strap attached to an end of the body and having several hook-and-loop fastener portions for leakless securing of the protector to the body member.

23 Claims, 7 Drawing Sheets

(56) References Cited

U.S. PATENT DOCUMENTS

| | | | |
|---|---|---|---|
| 5,188,608 | A | 2/1993 | Fritts |
| 5,342,286 | A | 8/1994 | Kelly et al. |
| 5,720,712 | A | 2/1998 | Joy et al. |
| 5,720,713 | A | 2/1998 | Hutchison |
| 5,817,038 | A | 10/1998 | Orange et al. |
| 6,053,170 | A | 4/2000 | Padilla, Jr. |
| 6,276,364 | B1 | 8/2001 | Warner |
| 6,664,434 | B2 * | 12/2003 | Cominsky ............. A61F 15/004 602/61 |
| 6,895,971 | B1 | 5/2005 | Evans |
| 9,820,880 | B1 | 11/2017 | Martin-Hill |
| 10,918,836 | B2 | 2/2021 | Jutras |
| 2004/0199092 | A1 | 10/2004 | Biewend et al. |
| 2005/0027227 | A1 | 2/2005 | Dumas et al. |
| 2007/0141126 | A1 * | 6/2007 | Hudson ................... A61L 2/22 424/443 |
| 2010/0240800 | A1 * | 9/2010 | Cunningham ....... C08K 5/0058 523/122 |
| 2012/0144547 | A1 * | 6/2012 | Collins .............. A41D 13/1236 2/67 |
| 2015/0290053 | A1 * | 10/2015 | Loughney ............ A61F 15/004 602/3 |

\* cited by examiner

WATERPROOF PROTECTOR FOR A BODY MEMBER

RELATED APPLICATION

The present application claims priority to or benefit of U.S. provisional patent application No. 63/219,510, filed Jul. 8, 2021, which is incorporated herein by reference in its entirety.

FIELD

The subject matter disclosed generally relates to protectors to be worn over a catheter insertion site, over a plaster or other wound dressing or over a limb. In particular, it relates to a waterproof protector to be worn for showering.

BACKGROUND

There are various protectors on the market for people having a catheter insertion site, a plaster (a bandage or other wound dressing) or a limb. For example, a plastic bag may be used, which is only suitable for body extremities, which is not reusable, not comfortable and easy to pierce. Commercial products using the same materials are found on the market, and can be used on body members other than extremities, but have the same drawbacks of lack of comfort, absence of reusability (often disposable), not conforming to body members (fluffy) and therefore in the way during showering, and easy to pierce. There are also plastic tubes which are not fluffy and which are made to form a tight plastic surface protection on the arm, but such devices are not comfortable to wear and can be very irritating on catheter insertion sites and the like, while also not being reusable, and having no particular antibacterial properties.

Other protectors on the market typically have other features which prevent obtaining satisfying waterproofness when taking a shower. For example, most tubular protectors are either made of an extrusion, and therefore are made of a material which is not breathable and typically are made of plastic sheets having the drawbacks mentioned above (only suitable materials to be extrudable). Tubular protectors which are not made of extrusions typically comprise stitching, which is permeable to water, or even zippers and the like, which are also permeable to water. Stiches, zippers and other similar elements may be provided in commercially-labelled "waterproof" versions, which are adapted to spilling but fail to have sufficient waterproofness when showering, and especially when movements are made during a shower, which deforms the materials forming the stiches or the zippers and allow water to enter.

There is therefore a need for a protector which is waterproof even when a person moves during a shower, while having a protector which is mechanically resistant, comfortable, elastic to allow freedom of movement, reusable, and not too fluffy to be in the person's way as in "plastic bag" types of protectors.

SUMMARY

It is an object of the present disclosure to provide a waterproof protector for a body member.

A waterproof protector for a body member and a method for fabricating the waterproof protector. The waterproof protector comprises a body comprising a fabric layer comprising polyester; a water repellent applied to a first surface of the fabric layer; an antimicrobial substance applied to an opposite surface of the fabric layer and located on an inner surface of the body. The body comprises a main seam formed by a junction of the fabric layer, the junction being sewn by an ultrasound to form a main seam which is further sealed with an additional layer of a waterproof material positioned on the inner surface of the body and sealed to the inner surface by heat. The waterproof protector further comprises a stretchable strap attached to an end of the body and having several hook-and-loop fastener portions for leakless securing of the protector to the body member.

According to another aspect of the disclosed technology, there is provided a waterproof protector which comprises a continuous surface that surrounds a body member, the continuous surface comprising, on an outer surface, a water repellent applied thereonto, and, on an inner surface, an antimicrobial agent applied thereonto, the continuous surface being formed of a fabric comprising polyester having a linear density between 20 D and 40 D, knitted at a surface density between 100 GSM and 130 GSM, the continuous surface comprises a junction of the fabric along a length of the protector which is sewn by ultrasound and further sealed to avoid stitching marks and be free of any piercing. In some embodiments, the water repellent is a polyurethane laminate. The antimicrobial agent may comprise 2-n-octyl-4-isothiazolin-3-one (OIT).

According to another aspect of the disclosed technology, there is provided a method for fabricating a waterproof protector, the method comprising: providing a panel of fabric comprising polyester having a linear density between 20 D and 40 D, knitted at a surface density between 100 GSM and 130 GSM, applying PUL on an outer side; applying OIT on an inner side as an antibacterial and antifungal finish; bringing together opposed edges of the panel of fabric, in a junction, to form a tube, the opposed edges overlapping very minimally to avoid forming a lip; performing ultrasound sewing using an ultrasound sewing machine on the junction to be sewn; adding a layer of waterproof material on the inner side including the junction, where said layer of waterproof material covers a seam formed at the junction by ultrasound sewing on the inner side; performing sealing with a hot air sealing machine which makes the added layer of waterproof material adhere onto the inner side of the protector along the seam; and securing a strap having Velcro™ hook-and-loop fastener portions onto of at least one end of the protector, the strap being for securing onto a body member and making a seal onto skin when secured onto the body member.

According to another aspect of the disclosed technology, there is provided a method for installing a waterproof protector onto a body member comprising the steps of: inserting the body member into the protector and reach a desired position for the protector onto the body member, to fit tightly on the body member and providing waterproofness, tightness further contributing to securing the protector on the body member; pulling on a strap of an end of the protector, stretching the strap and securing, to a base Velcro™ portion on said end, an opposing Velcro™ portion of the strap which the not most distal on the strap to hold the strap under tension in a first loop around a corresponding portion of the body member; further turning a remaining length of the strap, distally from the opposing Velcro™ portion, around the correspond part of the body member, while keeping about half the width of the strap continuously over said end and while keeping the other half of the width of the strap continuously over adjacent skin surface of the person, ensuring waterproofness of said end of the protector. The method may further comprise repeating the pulling on a strap and stretching the strap on another end of the protector. The method may further comprise repeating the step of turning the remaining length while keeping about half the width of the strap continuously over said end and while keeping the other half of the width of the strap continuously over adjacent skin surface of the person with the strap on said other end of the protector.

According to another aspect of the disclosed technology, there is provided a waterproof protector for a body member comprising: a body for surrounding the body member, the body having a continuous surface, the body comprising: a fabric layer comprising polyester; a water repellent applied to a first surface of the fabric layer; an antimicrobial substance applied to a second surface of the fabric layer and located on an inner surface of the body; the body comprising a junction of the fabric layer along a length of the body, the junction being sewn by ultrasound to form a main seam which is further sealed with an additional layer of a waterproof material, the additional layer being located on the inner surface of the body; and a strap attached to an end of the body, the strap being stretchable and having a first hook-and-loop intermediate fastener portion and a distal hook-and-loop fastener at a strap's edge, the strap having a strap's length or stretching and wrapping at least twice around the body member and for securing the strap to a base hook-and-loop portion located on the body member to the first hook-and-loop intermediate fastener portion and securing the distal hook-and-loop fastener to a second base hook-and-loop portion to secure the waterproof protector to the body member.

In at least one embodiment, the water repellent is a polyurethane laminate. The antimicrobial substance may comprise 2-n-octyl-4-isothiazolin-3-one (OIT). The antimicrobial substance may be at least one of a microbial repulsive substance and antibacterial and antifungal substance. The fabric layer may have a linear density between 20 D and 40 D, knitted at a surface density between 100 GSM and 130 GSM.

In at least one embodiment, the antimicrobial substance is incorporated into the fabric layer at a concentration between 0.1% and 0.75% in weight with respect to the weight of the fabric layer. The additional layer may cover the main seam and is sealed by hot air to the inner surface of the body of the waterproof protector.

The waterproof protector may further comprise a second strap attached to another end of the body, the second strap being elastic for stretching the second strap having another hook-and-loop fastener at a second strap's edge, the second strap having a second strap's length for stretching at least twice around the body member and securing the second strap to the body to secure the waterproof protector to the body member.

The waterproof protector may further comprise an extreme portion, the extreme portion being formed to have a shape of one of a boot and a mitten and having at least a portion of the main seam. The waterproof protector may further comprise a boot portion which has an anti-slip membrane attached to a sole of the boot portion.

According to another aspect of the disclosed technology, there is provided a method for fabricating a waterproof protector comprising: providing a panel, the panel having a fabric layer comprising polyester, applying polyurethane laminate (PUL) on an outer surface of the fabric layer; applying an antimicrobial substance on an inner surface of the fabric layer; bringing together opposed edges of the panel, in a junction, to form a body of the waterproof protector having a lumen; performing ultrasound sewing using an ultrasound sewing machine on the junction to form a main seam; adding an additional layer of a waterproof material on the inner surface to cover the main seam on the inner surface; performing sealing with a hot air sealing machine which makes the additional layer of the waterproof material to adhere onto the inner surface of the waterproof protector along the main seam; and securing a strap having hook-and-loop fastener portions onto at least one end of the waterproof protector, the strap being for securing onto a body member and making a seal onto the body member when secured onto the body member.

The antimicrobial substance may be OIT. In at least one embodiment, the opposed edges may be brought together by overlapping of less than 5 millimeters to avoid forming a lip. The antimicrobial substance may be incorporated into the fabric layer at a concentration between 0.1% and 0.75% in weight with respect to the weight of the fabric layer. The fabric layer may have a linear density between 20 D and 40 D, knitted at a surface density between 100 GSM and 130 GSM.

According to another aspect of the disclosed technology, there is provided a method for installing a waterproof protector onto a body member comprising the steps of: inserting the body member into the waterproof protector through a lumen provided by a body of the waterproof protector and reach a desired position for the waterproof protector onto the body member, to fit tightly on the body member and to provide waterproofness, tightness further contributing to securing the waterproof protector on the body member; pulling a strap attached to an end of the body of the waterproof protector, stretching the strap and securing, to a base hook-and-loop portion located on the end of the body of the waterproof protector, an opposing hook-and-loop portion located on the strap, the opposing hook-and-loop portion being located between a most distal hook-and-loop portion on the strap and the base hook-and-loop portion relative to the length of the strap, to hold the strap under tension in a first loop around the body member; further wrapping a remaining length of the strap around the body member, distally from the opposing hook-and-loop portion, around the body member, while positioning about half of a width of the strap continuously over the end of the body of the waterproof protector and while positioning the other half of the width of the strap continuously over adjacent skin surface of the body member, to prevent water from penetrating inside the lumen of the body of the waterproof protector during use.

The method may further comprise pulling on and stretching of another strap located on another end of the body of the protector to secure the another strap with hook-and-loop portions to attach the another strap to the body member and to hold the another strap under tension in another strap's loop around the body member. The method may further comprise: wrapping the remaining length of the another strap while positioning about half the width of the another strap continuously over the another end of the waterproof protector and while positioning the other half of the width of the another strap continuously over an adjacent skin surface of the body member with the another strap.

BRIEF DESCRIPTION OF THE DRAWINGS

Further features and advantages of the present disclosure will become apparent from the following detailed description, taken in combination with the appended drawings, in which:

FIG. 13 is a flowchart illustrating a method for fabricating the protector, according to at least one embodiment of the present disclosure;

FIG. 14 is a flowchart illustrating a method for installing the protector to have the end(s) thereof waterproof, according to at least one embodiment of the present disclosure;

FIG. 15A schematically illustrates a cross-sectional view of a panel of fabric when manufacturing the protector, in accordance with at least one embodiment of the present disclosure;

FIG. 15B schematically illustrates a cross-sectional view of the protector during the manufacturing, in accordance with at least one embodiment of the present disclosure; and FIG. 15C schematically illustrates a portion of the cross-sectional view of the protector, in accordance with at least one embodiment of the present disclosure.

It will be noted that throughout the appended drawings, like features are identified by like reference numerals.

DETAILED DESCRIPTION

There is described herein a protector (also referred to as a "waterproof protector") for a body member which prevents a liquid, typically water, to reach the body member, especially when a person is showering. Such a protector is typically worn over a catheter insertion site, a peripherical inserted central catheter (PICC) line, a plaster (such as a bandage or other or other wound dressing), a limb, or similar device on a person's body for which waterproofness is desirable. The protector as described herein is water-resistant when attached to the person's body member and may be used when the person is showering. When used herein, the term "waterproof", or impervious to water, means that the water would reasonably not penetrate through the protector towards the person's body member when the person is showering with the attached to the person's body member.

The protector as described herein may be designed with various parameters as described herein, including the nature of the fabric, linear density of the thread, surface density of its knitting, coating of the fabric, such fabric providing comfort and movability being not extrudable required a seam, and the seam is also made with different parameters including ultrasound welding of the fabric junction and dedicated sealing. The parameters as provided herein (and as described in more detail below) are an optimal trade-off between waterproofness for showering purposes while remaining comfortable, elastic, not easily pierced, and flexible enough to perform movements, such as the dynamic movements of the arm while showering (e.g., when applying shampoo in the hair), which require both unimpeded freedom of movement and waterproofness of the protector. The characteristics (parameters) of the fabric described herein and the use of such a fabric in the conditions as described below also allows washing and reusability. The protector as described herein can be washed and can be reused.

Figure 4:
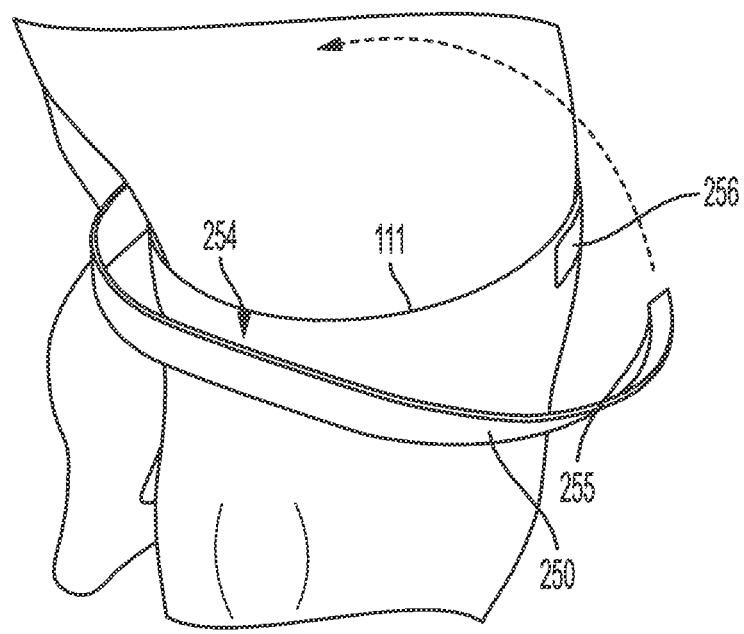
FIG. 4 is a perspective view showing a protector with a strap being stretched, with hook-and-loop fastener (Velcro™) portions for holding the strap stretched around the body member and securing the strap in a tight way, according to at least one embodiment of the present disclosure.
Figure 5:
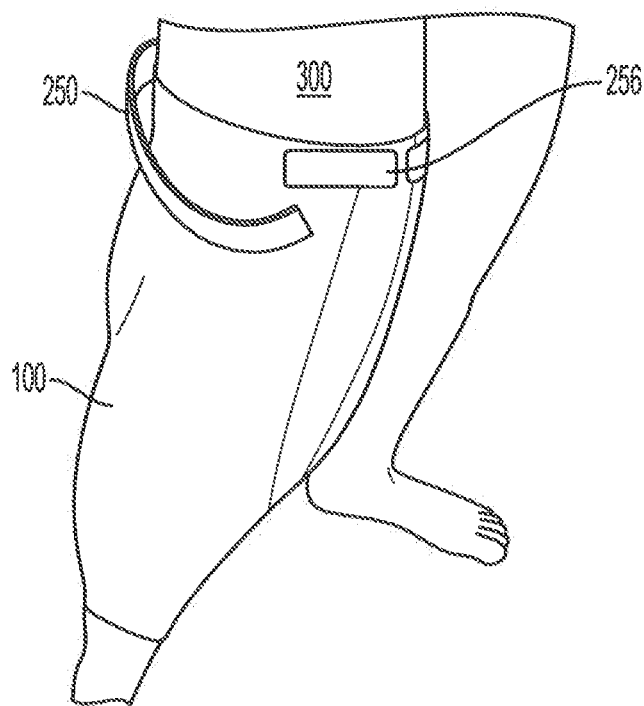
FIG. 5 is another perspective view showing the protector of FIG. 4.
Figure 6:
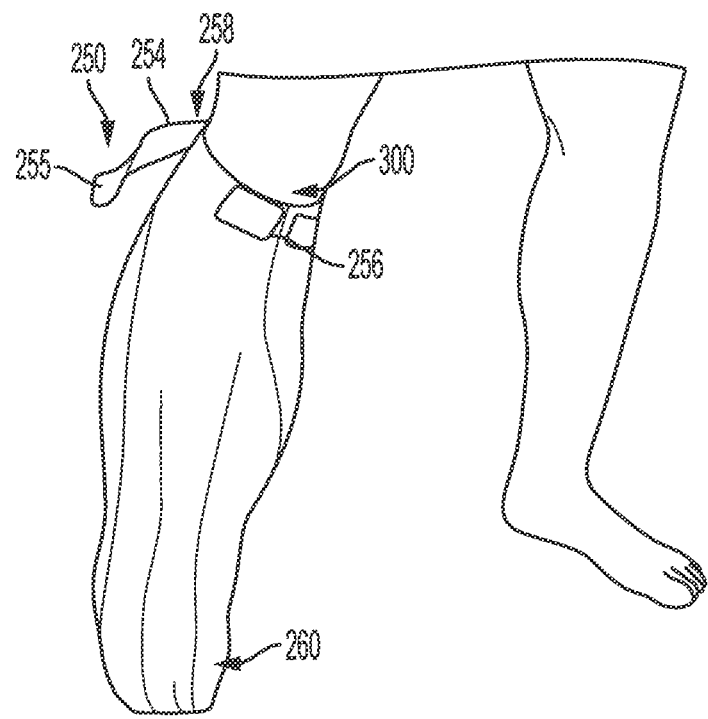
FIG. 6 is a perspective view showing a leg and foot protector (a similar protector could be for an arm and hand), with a strap being stretched, with hook-and-loop fastener (e.g., Velcro™) portions for holding the strap stretched around the body member and securing the strap in a tight way, according to at least one embodiment of the present disclosure.
Figure 7:
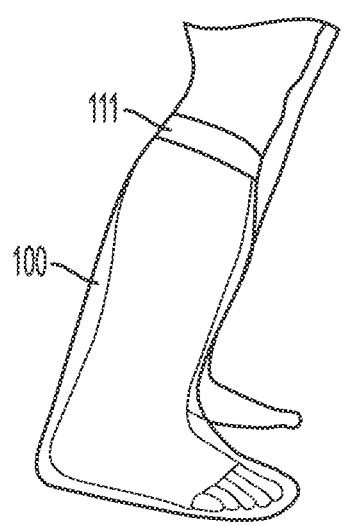
FIG. 7 is a perspective view showing a transparent leg and foot protector, according to at least one embodiment of the present disclosure.
Figure 8:
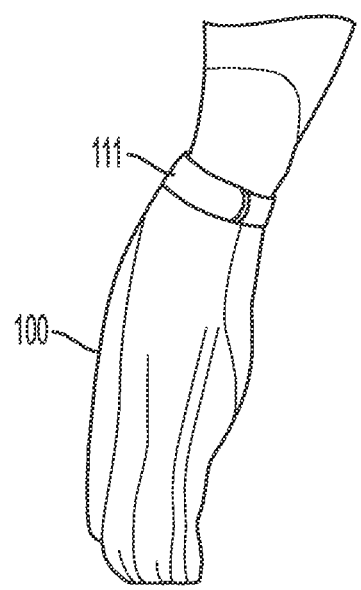
FIG. 8 is a perspective view showing a leg and foot protector as in FIG. 7, according to at least one embodiment of the present disclosure.
Figure 9:
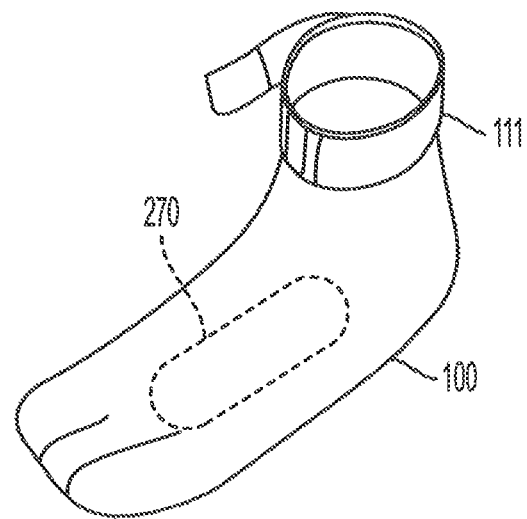
FIG. 9 is a perspective view showing a foot protector, according to at least one embodiment of the present disclosure.
Figure 10:
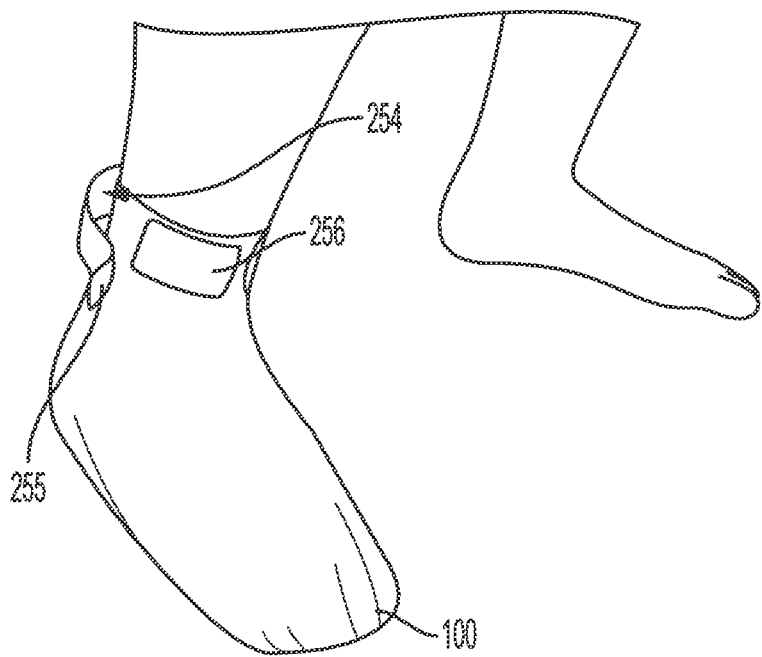
FIG. 10 is a perspective view showing a foot protector, with a strap being stretched, with hook-and-loop fastener (e.g. Velcro™) portions for holding the strap stretched around the body member and securing the strap in a tight way, according to at least one embodiment of the present disclosure.
Figure 11:
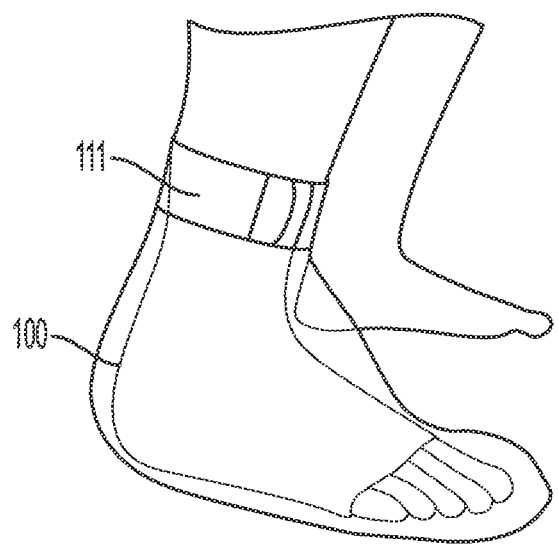
FIG. 11 is a perspective view showing a foot protector (transparent), according to at least one embodiment of the present disclosure.
Figure 12:
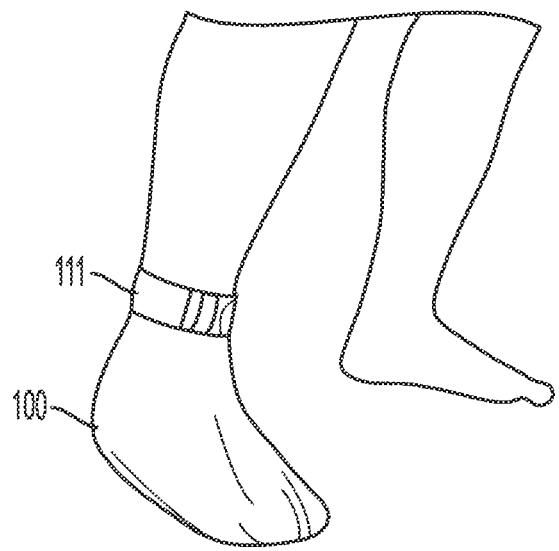
FIG. 12 is a perspective view showing a foot protector as in FIG. 11, according to at least one embodiment of the present disclosure.

FIGS. 1-12 illustrate various embodiments of a protector 100 having a continuous outer surface 116 providing waterproofness. FIGS. 1-5 show that the protector 100 can be open and installed on a leg, and the same protector or a very similar protector as the one shown in FIGS. 1-5 could be used on a person's arm in the same way. FIGS. 6-8 show a closed protector covering the lower leg portion of a person, which would be adequate for a person wearing a limb, for example and without limitation. FIGS. 9-12 show a closed protector installed on a foot.

The protector 100 comprises a continuous surface 110 (also referred to herein as "body 110") having an outer surface 116 (which may also be referred to as an "outer side of the body of the protector") and an inner surface 118 (which may also be referred to as an "inner side of the body of the protector").

The body 110 of the protector 100 is constructed to be continuous over the distance extending from a first end 111 to a second end 112. At least one of the ends, in particular the first end 111 (most proximal end to the person's trunk), is open, to insert the person's body member therein and through the inside lumen 113 of the protector 100. In at least one embodiment, the second end 112 (most distal end, or extreme end) may be closed if the person's body member is completely enclosed inside the protector 100 (e.g., of the body member is a hand or a foot, an as shown in FIGS. 6-13). The second end 112 may otherwise be open if the person's body member is inserted through the complete length of the protector 100, for example, if the protector 100 is installed on the arm or forearm or leg, with the hand or foot protruding out from the second end 112, as shown in FIGS. 1-5.

As well shown in FIGS. 1-13, the protector 100 forms a continuous and waterproof body 110 with the waterproof outer surface 116 from the first end 111 to the second end 112. The surface of the body 110 of the protector 100, which is continuous and waterproof, extending from the first end 111 to the second end 112, prevents water or other liquid from being spilled or splashed onto the surface of the person's body (including the person's skin). The outer surface 116 of the body 110 of the protector 100 is continuous and waterproof, while extending between the first end 111 and second end 112, which ensures that the whole body 110 is continuous and waterproof. This helps to avoid infiltration of the water or other liquid through the body 110 inside the lumen 113 of the protector 100. The inner surface 118 of the protector 100 is also continuous.

To ensure that the surface the body 110 is waterproof, according to an embodiment, different techniques are used. An appropriate material is used, as detailed below. The materials described below cannot be produced by extrusion and are provided as panels of fabric, which require sewing. An appropriate method for sewing the panel of fabric to form a cylindrical enclosure which has a waterproof seam is also described below. Also, the first end 111, and the second end 112 (if open) have a closure mechanism to ensure that water being splashed or spilled onto that part of the protector 100 (such as when the person is showering) does not enter into the protector by that end.

To ensure that the outside surface (as well as the inside surface) of the body 110 is continuous, the protector 100 is made of a single material, provided in a single part with no aperture and being seamless. To provide a seamless surface, the protector 100 would not to be fabricated by extrusion or a similar process, which is typical of plastic materials. A continuous surface of plastic (such as the plastic used in disposable plastic bags) is however not suited for the envisaged use, which is the protection of a body member while providing reasonable comfort to the wearer, since the use of a plastic would induce extreme sudation by the skin of the enclosed (protected) body member. Therefore, a breathable material other than a continuous surface of plastic (in particular the plastic used in plastic bags) is used in the protector 100 as described herein to avoid extreme sudation.

Suitable materials to achieve appropriate waterproofness, including elasticity to allow for natural movement of the body member, have been identified. The waterproofness may thus be maintained during the elastic stretching or displacement of the body 110 during the natural movement of the person's body member.

According to an embodiment, the material that is used to form the body 110 comprises polyester. According to at least one embodiment, the material used to form the body 110 of the protector has between 50% and 100% of polyester, between 80% and 100% polyester, preferably between 90% and 100% polyester, even more preferably 100% polyester.

According to an embodiment, the material is a knitted fabric, such as a knitted form of the polyester material listed above.

According to an embodiment, the knitted fabric uses fiber with a linear mass density comprised between 10 D and 70 D, more specifically between 15 D and 45 D, more specifically between 20 D and 40 D, more specifically between 25 D and 35 D, more specifically about 30 D. "D" denotes a denier which corresponds to the mass in grams per 9000 meters of the fiber used to knit the fabric used to make up the main body of the protector.

According to an embodiment, the fiber forming the fabric is knitted to reach a surface density (in grams per square meter or GSM) which is comprised between 80 GSM and 150 GSM, more specifically between 90 GSM and 140 GSM, more specifically between 100 GSM and 130 GSM, more specifically between 110 GSM and 120 GSM, more specifically about 114 GSM.

FIG. 15A schematically illustrates a cross-sectional view of a panel 140 of fabric when manufacturing the body of the protector, in accordance with at least one embodiment of the present disclosure. FIG. 15B schematically illustrates a cross-sectional view of the body 110, in accordance with at least one embodiment of the present disclosure. FIG. 15C schematically illustrates further details of a portion 130 of the cross-section depicted in FIG. 15B.

According to an embodiment, the fabric, which is used as a panel 140 for manufacturing protector 100, in addition to a fabric layer 142, further comprises a laminated material 145, in particular a water repellent, which is laminated thereonto. The laminated material 145 may be applied as a layer on one surface of the fabric (fabric layer 142 in FIG. 15C), or on both surfaces of the fabric (fabric layer 142 in FIG. 15C), or on significant portions of the fabric layer 142. According to an embodiment, the laminated material 145 is applied on the outside surface of the fabric 136 (also referred to herein as an "outside fabric layer surface 136" or "outer side of the fabric"), in other terms, the surface that may receive water during the use of the protector 100, which is directed away from the skin of the person wearing it. According to an embodiment, the water repellent forming the laminated layer of material is a polyurethane laminate (PUL), which is a water repellent which can be applied on the fabric while keeping the mechanical properties of the fabric suitable for wearing the fabric and moving the body part in an unobstructive manner.

According to an embodiment, the fabric used for body 110 of the protector 100 (in other terms, fabric layer 130) further comprises an antimicrobial and/or antifungal substance 147 (which may be also referred to as "antimicrobial substance 147" or "antimicrobial agent 147") added thereonto. This substance 147 may be antiseptic, i.e., killing microbes and preventing microbial growth. This antimicrobial substance 147 may also be a microbial repulsive substance, which repulses microbes and fungus to prevent microbes or fungus from adhering to the fabric if the substance is used in or on the fabric.

According to an embodiment, the antimicrobial and/or antifungal substance 147 is a solution of 2-n-octyl-4-isothiazolin-3-one (OIT). According to an embodiment, the solution of OIT is applied on the inner surface of the fabric 138, oriented toward the skin of the person wearing the protector 100 and opposite the water-repellent polyurethane laminate (or another laminated material 145). According to an embodiment, the solution of OIT may be incorporated into the substrate (fabric surface, in other terms fabric layer 142) at a concentration between 0.1% and 0.75% in weight with respect to the weight of the substrate (fabric surface, in other terms fabric layer 142) in which the OIT is incorporated. The panel 140 and the fabric (fabric layer 142) thereof may therefore be impregnated with the OIT with such a concentration (weight/weight), assuming impregnation across the thickness thereof and the whole surface. Otherwise, the OIT may impregnate mostly a minor, superficial depth of the fabric and act mainly on the surface where it is applied (inner surface).

Thus, the fabric panel 140 used for manufacturing the body 110 of the protector 100 has two surfaces: a first surface 116' that is waterproof (also referred to herein as a "waterproof surface") and the second surface 118' (which is preferably finished with Jersey also referred to herein as a "Jersey surface") and which has the antifungal substance 147 applied. When the body 110 of the protector 100 is formed, the second surface 118' of the fabric panel 140 is located inside the body 110 (for example, a tube) of the protector 100 and forms the inner surface 118 of the protector 100, while the waterproof surface 116' of the fabric is located outside of the body of the protector 100 and forms the outer surface 116 (illustrated in FIG. 1).

In at least one embodiment, the preferred fabric for the protector 100 may be Duoram Mm2820A, which is a 100% polyester fabric knitted Jersey 3 D (made of 100% polyester), polyurethane (PU) laminated, water-resistant (WR), waterproof (WP), antimicrobial and antifungal, 114 GSM, made from a 54"-wide panel.

In at least one embodiment, the fabric for the protector 100 may be Duoran-X149 or SilverBirch-2036A-200.

Microbiological tests were performed on an actual embodiment of the protector 100 which is constructed with the preferred parameters described above, i.e., a 100% polyester fabric using 30 D polyester fiber which is knitted ata density of 114 GSM, with PUL applied on the outer side and OIT applied on the inner side as an antibacterial and antifungal finish. The assessment of antibacterial and antifungal finishes on the textile material has shown the following results. Both a fabric sample and a seam sample (two samples each) were tested (the seam being described in greater detail below). The test was performed at a temperature of 28±1° C. for 7 days, where an inoculum was introduced onto the samples and tested for microbial growth. This was done on a sample which is new, and all tests were performed again on the samples after having undergone 5 cycles of cleaning in a washing machine. Bacterial growth was tested with a liquid inoculum of *Staphylococcus aureus* and a liquid inoculum of *Klebsiella penumoniae*. Fungal activity was tested with an inoculum of *Aspergillus niger* in the form of an agar slurry.

For all test variants mentioned above, the results were the same. The inoculum introduced in the first place, at time zero, did not adhere to the fabric or seam, and curled up right after the inoculum was tentatively introduced onto the sample. Protectors 100 with the body 110 made of the fabric Duoran-X149 have been tested. In another set of tests, protectors 100 with the body 110 made of fabric SilverBirch-2036A-200 have been tested. Following tests performed during 24 hours after introduction of the inoculum were consistent as they showed absence of any microbial activity, even after 24 hours following the instruction of the inoculum. Therefore, the test results show that the antibacterial and antifungal finishes on the textile material provide very effective protection against microbial growth.

According to an embodiment, the material is initially provided as a panel of fabric, for example a 54"-wide panel, which is cut and curved onto itself to form a tube, which can have a shape such as a cylinder or a truncated cone. This means that the initially planar panel of fabric has opposite ones of its edges brought one against the other, and the pair of opposed edges brought together are secured together in a waterproof way.

According to an embodiment, the opposed edges brought together are secured together by sewing them together. However, conventional sewing is not appropriate, since the conventional seam would not be waterproof, especially under running water (e.g., when the person is showering and the seam is directly exposed to water).

Also, having the junction of fabric being folded onto itself, as proposed in prior art protectors, for greater waterproofness is also inappropriate in the present context (technology) as it introduces rigidity along the protector 100.

Also, folded fabric inside the protector 100 makes it thicker at that location, i.e., a lip is formed which is not comfortable, and folded fabric outside the protector 100 makes it bothersome (the lip of folded fabric being in the way when the person wearing the protector moves their arm or leg). Therefore, folded fabric at the junction is avoided in the embodiments of the protector 100 as described herein, in addition to avoiding the conventional sewing, as mentioned above.

Figure 1:
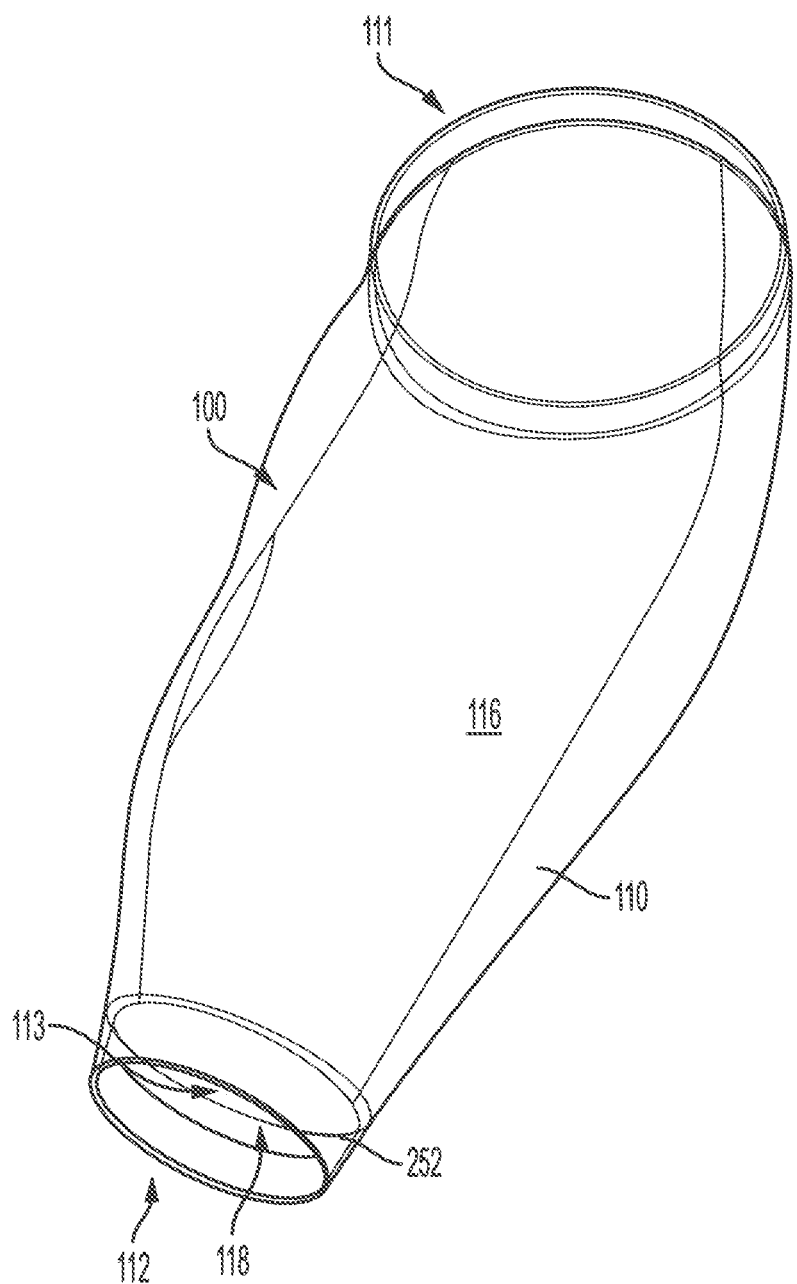
FIG. 1 is a perspective view showing a protector having both open ends (arm protector or leg protector), according to at least one embodiment of the disclosure.

According to an embodiment of the present disclosure, to join together the opposed edges brought together and form the tubular shape which is best shown in FIG. 1 and preserve the waterproofness of the whole surface of the body 110, the main seam 155 (also referred to as a "junction" and indicated in FIG. 15B) is formed by the process as described herein using ultrasound sewing by an ultrasound sewing machine. The protector 100 has mechanical integrity of the main seam 155 (i.e., the edges being solidly joined together including when the user moves significantly) and maintains waterproofness during movement including during the normal stretching of the material of the protector. To achieve comfort on the person's skin, for example, there is no inner protruding lip or portion of fabric which would irritate the person's skin especially when the user is moving. Thus, the junction 155 of the fabric is located along a length of the protector 100 and is sewn by ultrasound and further sealed to avoid stitching marks and be free of any piercing.

Ultrasonic sewing is like welding two pieces of fabric together. The result is very durable, and provides stitching without having sewing thread through the fabric, which would otherwise make it less waterproof (i.e., the sewing thread would make it leaky). Instead, the joined material is fused without having to pierce it.

Ultrasonic sewing is performed by passing high-frequency vibrations between 20 kHz up to 70 kHz. When the thermoplastic material passes between the sonotrode and the anvil, these vibrations create rapid heating. This heat melts the thermoplastic material (such as polyester) which is welded at the place where the heat is applied, preferably at a junction of such material.

Generally, an ultrasound sewing machine comprises the following elements:
a) A power unit that takes electricity from the grid at 50 or 60 cycles per second and converts it to a high ultrasonic frequency between 20,000 to 70,000 cycles per second.
b) A converter containing piezoelectric crystals which convert the incoming high frequency electrical signal into mechanical vibrations.
c) A booster (or amplifier) that transmits vibrational energy and increases its amplitude, much like an electrical transformer changes voltage.
d) A sonotrode which transmits the energy of vibration to the thermoplastic material to be worked.
e) An anvil or support that supports the piece.

Textile materials: the materials used can be 100% synthetic or combinations of materials comprising up to 40% natural fibers. Nonwovens, woven fabrics, elastic woven fabrics or knits can all be glued and cut or incised. Acrylic, acetates, polyester, nylon, polyethylene, spandex and polyvinyl chloride (PVC) are all suitable for fusing and cutting by the ultrasound sewing machine. In general, the higher the synthetic content, the better the material will be suitable for welding (by fusion of the plastic material) with ultrasonic energy. Some materials can be bidirectional, that is, fibers in one direction have a different composition than fibers in the other direction.

Stitching machine: the most frequently used machine is the Seamstar™. Such a stitching machine can simulate single, double or triple lines of stitching marks. It should be noted that the ultrasound sewing machine, when fusing two portions of fabric together, does not produce stitching marks as the fabric is not pierced. The available stitch patterns of the stitching machine include dashed lines, dotted lines, single stitches, double stitches, zigzag, lock stitches, hem stitches, stem stitches and lace stitches as well as flower and lace patterns, leaves. The designs are machine-made or engraved in the rotating anvil.

Cylinder machines are available in both an offset arm version and a side arm version. Cylinder machines use a cylindrical arm equipped with a rotating wheel and an ultrasonic system above the wheel. The fabric is introduced between the wheel and the sonotrode. The side arm configuration can be used to weld collars or cuffs or to put elastic in pant legs, in cuffs or the like. Once again, a variety of designs are available, ranging from a single row up to 3 rows of stitches or solid lines. The offset arm model is used for the manufacture of any tube-shaped product, such as for example sleeves, trouser legs or tubes, as contemplated herein.

To ensure proper fusing of the material at a junction 150 (FIG. 15A) being sewn or welded, the heating may be sufficient (while the temperature is not higher than about 350° C.) and it should be uniform in time and space as the junction 150 is made to ensure that the ultrasound-made stitch is uniform along the junction. According to an embodiment, the temperature of fusion of the material (fabric) is between 250° C. and 450° C., preferably between 300° C. and 400° C., even more preferably at about 350° C.

Referring to FIGS. 1-12, the protector 100 has one or two straps 250. One strap 250 is located at first end 111 and, in some embodiments, another strap 250 is located at the second end 112 of the protector 100. The strap 250 is attached to the body 110 of the protector 100. In at least one embodiment, the strap 250 is stretchable by, for example, being made of a stretching material (material that may temporarily extend the length of the strap 250 when pulled by one or both ends).

As illustrated, the strap 250 contours the protector 100 at the edge of the proximal first end 111. The strap 250 has one or more hook-and-loop intermediate fastener portions 254 (such as, for example, Velcro™) and a distal hook-and-loop portion 255 (such as, for example, Velcro™).

In at least one embodiment, the strap 250 has a base hook-and-loop portion 256 (for example, Velcro™), male or female, on the edge of the distal end 112, as illustrated in FIG. 6. The base hook-and-loop portion 256 may be located on the distal end 112 of the protector 100. The strap 250 also has an opposing portion of hook-and-loop loose fastener 254 (for example, Velcro™), respectively female or male, which is not the most distal hook-and-loop portion on the strap 250. When the hook-and-loop loose fastener portion 254 is attached to the base hook-and-loop portion 256, they both hold, at least temporarily, the strap 250 under tension in a first loop around the corresponding portion of the body member. When the strap 250 is wrapped about the body 110 of the protector and the body member for the second turn, at least one other pair of the hook-and-loop portions (male and female), when attached to each other, may hold the strap 250 under tension and attach the protector 100 to the person's body member.

The strap 250 may be attached to the body 110 partially at one end so that the strap 250, when wrapped about the body member may have about half the width of the strap continuously over the end of the body 110 and simultaneously have the other half of the width of the strap 250 continuously over adjacent skin surface of the person, ensuring waterproofness of the end of the protector 100.

In at least one embodiment, the strap 250 is attached to an end of the body and is elastic for stretching. The strap 250 may be positioned on the body 110 to be capable to be partially positioned on the body member along a strap's length. The strap 250 has a strap's length for stretching and wrapping at least twice around the body member and for securing the strap 250 to the body member (the base hook-and-loop portion 256) with the first hook-and-loop intermediate fastener portion 254 and the distal hook-and-loop fastener 255 at a strap's edge to secure the waterproof protector to the body member. The distal hook-and-loop fastener 255 is secured to a second base hook-and-loop portion 258 which may be located, for example, of the strap 250, but on an opposite side (surface) of the strap 250 with regard to the distal hook-and-loop fastener 255 to be capable to fasten with the distal hook-and-loop fastener 255 when wrapped about the body member.

Figure 2:
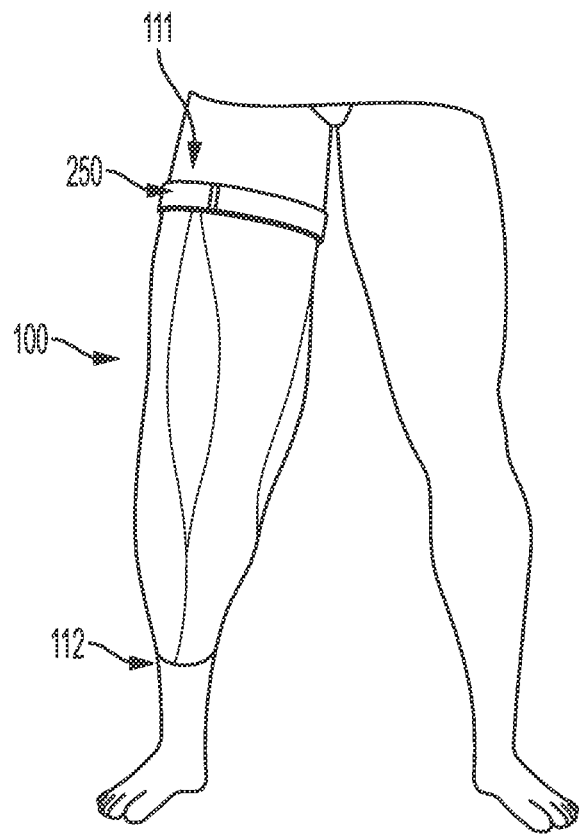
FIG. 2 is a perspective view showing a leg protector (a similar protector could be for an arm), according to at least one embodiment of the present disclosure.
Figure 3:
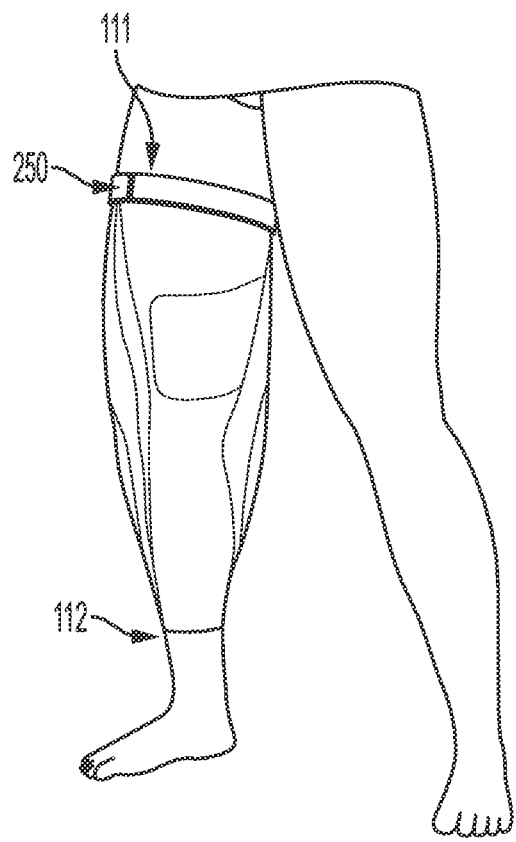
FIG. 3 is a perspective view showing a transparent leg protector (a similar protector could be for an arm), according to at least one embodiment of the present disclosure.

FIGS. 2, 3, 5 show the protector 100 with a tube's shape and without any extreme portion such as, for example, a boot portion or a mitten portion. FIGS. 6-7 illustrate the protector 100 with a boot portion 260 which has a shape of a boot. If the protector 100 does not have any boot portion 260, such embodiment of the protector 100 is illustrated in FIGS. 1-3, a second strap 252 may be located at the distal second end 112. The strap 250 is secured onto the person's body member. Such straps 250, when attached (secured) to the person's body member (a hand or a leg), seal the protector 100 to the person's skin of the body member.

According to an embodiment, a zigzag machine is used to lay an elastic grip with silicone. This gripping layer of silicone laid down on the surface of the upper portion of the protector 100 oriented toward the wearer's skin ensures antiskid properties to the elastic band. This silicone layer on the inner (contacting) surface of the fabric can have a zigzag (alternating up and down) pattern all around the inner surface of a perimeter of an upper portion of the protector 100.

In some embodiments, the protector 100 of a boot shape (as illustrated in FIGS. 9-12) and the protector 100 with a boot portion 260 (as illustrated in FIGS. 6-7) has a self-adhesive and anti-slip membrane 270 which is fixed underneath on the sole to prevent person (user, patient) from slipping and injuring themselves.

Now referring to the flowchart of FIG. 13, it is shown that the method 1000 of fabrication of the protector 100, including the joining process described above, comprises the steps of:

Step 1100: providing a panel of fabric with parameters as described above, such as (for example and without limitation) the preferred parameters described above, for example, a 100% polyester fabric using 30 D polyester fiber which is knitted at a density of 114 GSM, with PUL applied on the outer side (surface) and OIT applied on the inner side as an antibacterial and antifungal finish;

Step 1110: bringing together the opposed edges of the panel 140 of fabric, the edges being aligned side-by-side, as illustrated in FIG. 15A, and overlapping very minimally at the junction 150 to avoid forming a lip or other form of folded fabric which makes this part thicker, and forming an appropriate shape for the protector 100, such as, without limitation, a tube, truncated cone, tube with closed distal end for housing a hand or a foot, etc.;

Step 1120: performing ultrasound sewing using an ultrasound sewing machine on the junction 150 to be sewn (schematically illustrated with an arrow 152), by avoiding making a lip of folding the fabric and making the main seam 155 as smooth as possible;

Step 1130: adding an additional layer 160 of a waterproof material on the inner side of the surface (in other terms, on the inner surface 118) as illustrated in FIG. 15B including the join (junction 155), where the additional layer 160 covers (fully covers) the main seam 155 (junction 155) formed between the joined edges on the inner side thereof;

Step 1140: performing sealing with a sealing machine, such as a hot air sealing machine which makes the added additional layer 160 of the waterproof material adhere onto the inner side (inner surface 118) of the protector 100 along the ultrasound sewn junction (main seam 155) which closes the protector 100 to form a tubular shape and/or shape of a foot or hand or another shape of the protector 100 as described herein;

Step 1150: securing the strap 250 having hook-and-loop fastener portions 254, 255, 256 (for example, Velcro™) onto the contour of at least one end of the protector 100, preferably at the edge of both the proximal first end 111 and distal second end 112, the strap 250 being for securing onto the body member and making a seal onto (in other words, sealing the protector 100 to) the person's skin when secured onto the person's body member.

In some embodiments, step 1100 may comprise providing a fabric panel having a fabric layer comprising polyester and applying PUL on an outer surface of the fabric layer. The antimicrobial substance may then be applied to the inner surface of the fabric layer.

According to an embodiment, a zigzag machine is used to lay an elastic grip with silicone. For a protector 100 of a boot shape, a self-adhesive and anti-slip membrane is fixed underneath on the sole to prevent person (user, patient) from slipping and injuring themselves.

At steps 1130 and 1140, according to an embodiment, there is used a seal machine which is also known as a hot air sealing machine. The hot air sealing machine is a machine which heats air and outputs it onto a strip of plastic material (i.e., the added layer of waterproof material) which makes it adhere to the underlying surface as long as there is compatibility between the materials to provide the adherence. Typically, the hot air sealing machine would have dedicated strips of plastic-containing material (a textile), which would adhere to the polyester or similar fabric used for the body of the protector 100.

When forming the shape of the protector 100 at step 1110, the Jersey surface of the fabric is positioned inside the body 110 of the protector 100, while the waterproof surface of the fabric is positioned outside of the body 110 of the protector 100. The fabric, prior to forming the shape of the protector 100, is treated with an antiseptic and antifungal substance (as described above) such that the internal surface which is Jersey surface has antiseptic and antifungal properties.

The additional layer 160 attached to the inner surface 118 to cover the main seam 155 of the protector 100 may therefore cover the main seam 155 and leave sufficient area of the fabric layer 142 uncovered with the additional layer 160 in order to have sufficient exposure of the antifungal substance 147 towards the surface of the person's body member (skin).

The strap 250, when attached to the body 110 of the protector 100, provides a water barrier and ensures sealing of the protector 100 to the person's body. The protector 100 may have one or two straps 250. The length of the strap 250 is such that it permits to make more than two turns around the protector 100 installed on the person's body member 300 (see FIG. 6). At least one strap 250 is longer than two turns around a person's body member to secure the protector 100 to the person's body member.

When forming a body 110 (for example, of a tube shape) with the opposed edges of the panel 140, the opposed edges may overlap by, for example, 1 centimetre or less. Preferably, the opposed edges of the panel 140 are overlapping by less than about 5 millimeters (i.e., between about 0 and about 5 mm), more specifically between about 2 and about 4 millimeters. Now referring to a method for installing the protector according to an embodiment, as shown in the flowchart of FIG. 14, the method comprises the steps of:

Step 2110: inserting the body member into the protector and reach the desired position for the protector onto the body member, which according to an embodiment, is the maximum, farthest possible position on the body member that the protector can reach, having an inner diameter of its proximal end (first end 111) which corresponds to the diameter of the farthest possible position on the body member that the protector can reach, thereby making the inner diameter of its proximal end (first end 111) fit very well and tightly on the body member and providing waterproofness, the tightness further contributing to securing the protector 100 on the body member;

Step 2120: pulling on the band or strap 250 of the distal end, i.e., the second end 112 (e.g., close to the wrist in the case of an arm protector, close to the ankle in the case of a leg protector), stretching it and securing, to a base hook-and-loop (Velcro™) portion 256 (male or female) on the edge of the distal end 112, an opposing portion of the hook-and-loop fastener portion 254 (for example, made of Velcro™), respectively female or male, which is not the most distal hook-and-loop (Velcro™) portion on the strap 250 to hold, at least temporarily, the strap 250 under tension in a first loop around the corresponding portion of the body member. The strap 250 has at least two Velcro™ portions, a distal Velcro™ portion 255 located at the most distal portion of the strap 250 and at least one mid-section Velcro™ portion 254 located in between of the distal Velcro™ portion and an area of attachment of the strap 250 to the body 110.

In at least one embodiment, the strap 250 located at a first end 111 makes 3 turns around the body member (for example, the strap of the first end 111 located next to the person's knee makes 3 turns, or wraps, around the person's led). When the protector 100 is used with an arm, the strap 250 is long enough to make 3 turns around biceps and another strap of the protector 100, located towards the wrist, is long enough to make 2 turns around the person's wrist area before fixing on the Velcro™.

In at least one embodiment, the strap 250 is positioned such that when the strap is turned around the body member, approximately half (between about 40% and about 60%) of the strap 250 is located on the fabric of the body 110 (surface 110) and the other approximately half (between about 40% and about 60% and complementary to the first range) of the strap 250 on the skin of the body member. In at least one embodiment, after the base hook-and-loop portion 256 is attached to a first hook-and-loop intermediate fastener portion 254 (opposing hook-and loop fastener portion 254), the remaining length of the strap 250 is wrapped about the body member, distally from the first hook-and-loop intermediate fastener portion 254, around the part of the body member, while positioning about half the width of the strap 250 continuously over the end of the body of the waterproof protector and while positioning the other half of the width of the strap continuously over adjacent skin surface of the person FIG. 4, 6, 10 shows (proximal end equivalent) the pulling/stretching and turning of the strap 250 and also shows an example of the not-distalmost Velcro™ hook-and-loop fastener portion 254 on the strap 250 which, after such stretching of the strap 250, is expected to reach the base Velcro™ portion 256 to perform the first securing of the strap 250 with a remaining distal length of strap 250 to be acted upon in step 2130.

Step 2130: further turning the remaining length of the strap 250 (distally from the not-distalmost Velcro™ portion that was first used on the strap 250) of the distal, second end 112, around the correspond part of the body member. The length of the strap 250 is designed to be sufficient to make more than one turn around the body member (and preferably two, or more generally between 1 and 3 turns, and this feature should be inferred from FIGS. 4-5 by considering that the strap 250 is elastic and can and should be lengthened from what is shown in the image), while keeping about half the width of the strap 250 continuously over the proximal or distal end and while keeping the other half of the width of the strap 250 continuously over the adjacent skin surface of the person, maintaining this distribution of the strap's width (about half on the protector's end/edge and half on the skin) along the length of the strap 250 being turned around the body member. This distribution ensures waterproofness of the protector's distal second end 112. As shown in FIG. 4, 6, 10, there should be more portions of Velcro™ hook-and-loop fastener 255 along the length of the strap 250 distally from the already-used portion of Velcro™ hook-and-loop fastener secured to the base Velcro™ portion 256.

Step 2140: Same as step 2120, with the proximal end (first end 111) (using same reference numerals on the figures);

Step 2150: Same as step 2130, with the proximal end (first end 111) (using same reference numerals on the figures).

Methods should be adjusted to take into account that step pertaining to the distal end 112 may be removed from the methods if the protector 100 is without any open distal end (e.g., covering a foot as in FIGS. 6-12).

This method for installing the protector 100 ensures efficient waterproofness for heavy water spilling, such as when the person is showering while having a portion of a body member to protect (e.g., catheter insertion site, plaster, wound dressing, etc.). This may however not be suitable for bathing or swimming, as the protector 100 is instead designed to be an optimal trade-off between waterproofness for showering purposes while remaining comfortable, elastic and flexible enough to perform movements, such as the dynamic movements of the arm while showering (e.g., when applying shampoo in the hair), which require both unimpeded freedom of movement and waterproofness of the protector. The waterproofness is obtained both at the entry of the protector by installing it with the method described above, and on the protector surface, even if the protector is stretched or under torsion or shearing forces during body member movements, using the parameters described above. The properties such as waterproofness and antimicrobial activity are also maintained over time as the protector is washed repeatedly, making the protector reusable for long-term use.

According to a preferred embodiment of the disclosure, the protector 100 as described herein may be hand washed with mild soap and rinsed, and hanged for drying, instead of being washed in a washer or dried in a dryer. The material of the protector 100 should also be washed without chlorine.

The attachment with the elastic straps which have several hook-and-loop fastener portions as described herein permits to secure the protector 100 to the body member help to reduce leakage of the water or other liquids during showing (or rain, for example) thus helping to provide leakless securing of the protector to the body member.

The waterproof protector for a body member (such as, for example, a leg or an arm) comprises a body 110 for surrounding the body member, the body having a continuous surface. In at least one embodiment, the body 110 comprises: a fabric layer comprising polyester; a water repellent applied to a first surface of the fabric layer; an antimicrobial substance applied to a second surface of the fabric layer and located on an inner surface of the body. The body also comprises a junction of the fabric layer along a length of the body, the junction being sewn by ultrasound to form a main seam which is further sealed with an additional layer of a waterproof material, the additional layer being located on the inner surface of the body; and a strap attached to an end of the body, the strap being stretchable and having a first hook-and-loop intermediate fastener portion and a distal hook-and-loop fastener at a strap's edge, the strap having a strap's length for stretching and wrapping at least twice around the body member and for securing the strap to a base hook-and-loop portion located on the body member to the first hook-and-loop intermediate fastener portion and securing the distal hook-and-loop fastener to a second base hook-and-loop portion to secure the waterproof protector to the body member. In at least one embodiment, the fabric layer may have a linear density between 20 D and 40 D, knitted at a surface density between 100 GSM and 130 GSM.

The waterproof protector may further comprise the second strap 252 attached to another end 112 of the body member. The second strap 252 may be elastic for stretching the second strap 252 around the body member. The second strap 252 may have another hook-and-loop fastener at a second strap's edge, similar to the construction of the strap 250 illustrated in FIGS. 4-5. The second strap 252 may have a second strap's length for stretching at least twice around the body member and securing the second strap 252 to the body to secure the waterproof protector to the body member.

The waterproof protector 100 may comprise an extreme portion. The extreme portion may be formed to have a shape of one of a boot and a mitten and have at least a portion of the main seam. The waterproof protector 100 may have a boot portion with the anti-slip membrane attached to the sole of the boot portion.

In at least one embodiment, a method for fabricating a waterproof protector comprises: providing a panel, the panel having a fabric layer comprising polyester, applying PUL on an outer surface of the fabric layer; applying an antimicrobial substance on an inner surface of the fabric layer; bringing together opposed edges of the panel, in a junction, to form a body of the waterproof protector having a lumen; performing ultrasound sewing using an ultrasound sewing machine on the junction to form a main seam; adding an additional layer of a waterproof material on the inner surface to cover the main seam on the inner surface; performing sealing with a hot air sealing machine which makes the additional layer of the waterproof material to adhere onto the inner surface of the waterproof protector along the main seam; and securing a strap having hook-and-loop fastener portions onto at least one end of the waterproof protector, the strap being for securing onto a body member and making a seal onto the body member when secured onto the body member. In at least one embodiment, the opposed edges are brought together by overlapping of less than 5 millimeters to avoid forming a lip.

In at least one embodiment, to install the waterproof protector onto a body member, the following steps may be performed: inserting the body member into the waterproof protector through a lumen provided by a body of the waterproof protector and reach a desired position for the waterproof protector onto the body member, to fit tightly on the body member and to provide waterproofness, tightness further contributing to securing the waterproof protector on the body member; pulling a strap attached to an end of the body of the waterproof protector, stretching the strap and securing, to a base hook-and-loop portion located on the end of the body of the waterproof protector, an opposing hook-and-loop portion located on the strap, the opposing hook-and-loop portion being located between a most distal hook-and-loop portion on the strap and the base hook-and-loop portion relative to the length of the strap, to hold the strap under tension in a first loop around the body member; further wrapping a remaining length of the strap around the body member, distally from the opposing hook-and-loop portion, around the body member, while positioning about half of a width of the strap continuously over the end of the body of the waterproof protector and while positioning the other half of the width of the strap continuously over adjacent skin surface of the body member, to prevent water from penetrating inside the lumen of the body of the waterproof protector during use. Then, another strap (second strap 252) located on another end of the body of the protector may be pulled on and stretched to secure the second strap 252 with hook-and-loop portions to attach the second strap 252 to the body member and to hold the second strap 252 under tension in a loop around the body member. The remaining length of the second strap 252 may be wrapped while positioning about half the width of the second strap 252 continuously over the second end 112 of the waterproof protector 100 and while positioning the other half of the width of the second strap 252 continuously over an adjacent skin surface of the body member with the second strap 252.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A waterproof protector for a body member, comprising:
a waterproof body sized and shaped for surrounding the body member, the waterproof body having a first body end, a second body end, and a polyester fabric sheet having an outer surface and an inner surface, the fabric sheet extending between the first body end and the second body end, the fabric sheet defining a lumen of a size sufficient to receive therein the body member, the first body end having a first body end opening sized and shaped to receive therethrough the body member, the polyester fabric sheet having a main seam to which a waterproof seam layer is sealed, the polyester fabric sheet being a knitted fabric of a fiber having a linear mass density of between 20D and 40D, the knitted fabric having a surface density of between 100 GSM and 130 GSM;
a water repellent layer laminated to one or both of the outer and inner surfaces, the inner body surface having an antimicrobial substance applied thereto;
a first stretchable strap connected to one of the first or second body ends, the first stretchable strap having a first strap end portion, the first stretchable strap having a first hook-and-loop fastener, and one or more second hook-and-loop fasteners; and
a base hook-and-loop fastener located on either of the first or second body ends for engaging with at least one of the first hook-and-loop fastener and the one or more second hook-and-loop fasteners for securing the waterproof body to the body member.

2. The waterproof protector of claim 1, wherein the water repellent layer is a polyurethane laminate.

3. The waterproof protector of claim 1, wherein the antimicrobial substance includes 2-n-octyl-4-isothiazolin-3-one (OIT).

4. The waterproof protector of claim 1, wherein the antimicrobial substance includes at least one of a microbial repulsive substance and an antibacterial substance and an antifungal substance.

5. The waterproof protector of claim 1, wherein the antimicrobial substance is incorporated into the fabric layer at a concentration between 0.1% and 0.75% in weight with respect to the weight of the fabric layer.

6. The waterproof protector of claim 1, wherein the waterproof seam layer covers the main seam and is heat sealed to the inner surface of the polyester fabric sheet.

7. The waterproof protector of claim 1, further including a second stretchable strap connected to the second body end, the second stretchable strap having a second strap edge, a third hook-and-loop fastener connected to the second strap edge, the second stretchable strap having a length sufficient to stretch at least twice around the body member so as to secure the waterproof protector to the body member.

8. The waterproof protector of claim 1, wherein the second body end is closed to define an extreme end portion having at least a portion of the main seam, the extreme end portion being shaped to define a boot or a mitten.

9. The waterproof protector of claim 8, the boot includes an anti-slip membrane attached to a sole of the boot portion.

10. The waterproof protector of claim 1, wherein the polyester fabric sheet includes between 50% polyester and 100% polyester; between 80% polyester and 100% polyester; and between 90% polyester and 100% polyester.

11. The waterproof protector of claim 10, wherein the polyester fabric sheet is 100% polyester.

12. A waterproof protector for a body member, comprising:
a waterproof body sized and shaped for surrounding the body member, the waterproof body having a first body end, a second body end, and a polyester fabric sheet having an outer surface and an inner surface, the fabric sheet extending between the first body end and the second body end, the fabric sheet defining a lumen of a size sufficient to receive therein the body member, the first body end having a first body end opening sized and shaped to receive therethrough the body member, the polyester fabric sheet having a main seam to which a waterproof seam layer is sealed, the polyester fabric sheet being a knitted fabric of a fiber having a linear mass density of between 10D and 70 D, the knitted fabric having a surface density of between 80 GSM and 150 GSM;
a water repellent layer laminated to one or both of the outer and inner surfaces, the inner body surface having an antimicrobial substance applied thereto;
a first stretchable strap connected to one of the first or second body ends, the first stretchable strap having a first strap end portion, the first stretchable strap having a first hook-and-loop fastener, and one or more second hook-and-loop fasteners; and a base hook-and-loop fastener located on either of the first or second body ends for engaging with at least one of the first hook-and-loop fastener and the one or more second hook-and-loop fasteners for securing the waterproof body to the body member.

13. The waterproof protector of claim 12, wherein the linear density is between 15D and 45D; between 20D and 40D; and between 25D and 35D.

14. The waterproof protector of claim 13, wherein the linear density is about 30D.

15. The waterproof protector of claim 12, wherein the surface density is between 90 GSM and 140 GSM; between 100 GSM and 130 GSM; and between 110 GSM and 120 GSM.

16. The waterproof protector of claim 15, wherein the surface density is about 114 GSM.

17. The waterproof protector of claim 12, wherein the polyester fabric sheet includes between 50% polyester and 100% polyester; between 80% polyester and 100% polyester; and between 90% polyester and 100% polyester.

18. The waterproof protector of claim 17, wherein the polyester fabric sheet is 100% polyester.

19. The waterproof protector of claim 12, wherein the antimicrobial substance is incorporated into the fabric layer at a concentration between 0.1% and 0.75% in weight with respect to the weight of the fabric layer.

20. The waterproof protector of claim 12, wherein the waterproof seam layer covers the main seam and is heat sealed to the inner surface of the polyester fabric sheet.

21. The waterproof protector of claim 12, further including a second stretchable strap connected to the second body end, the second stretchable strap having a second strap edge, a third hook-and-loop fastener connected to the second strap edge, the second stretchable strap having a length sufficient to stretch at least twice around the body member so as to secure the waterproof protector to the body member.

22. The waterproof protector of claim 12, wherein the second body end is closed to define an extreme end portion having at least a portion of the main seam, the extreme end portion being shaped to define a boot or a mitten.

23. The waterproof protector of claim 22, in which the boot includes an anti-slip membrane attached to a sole of the boot portion.

\* \* \* \* \*